(12) United States Patent  
Arnold

(10) Patent No.: US 7,935,480 B2  
(45) Date of Patent: May 3, 2011

(54) DETECTION OF NUCLEIC ACID MUTATIONS BY DETECTING THE PRESENCE OF HETERODUPLEXES

(75) Inventor: Catherine Arnold, London (GB)

(73) Assignee: Health Protection Agency, London, Great Britain (GB)

( * ) Notice: Subject to any disclaimer, the term of this patent is extended or adjusted under 35 U.S.C. 154(b) by 709 days.

(21) Appl. No.: 11/722,703

(22) PCT Filed: Dec. 23, 2005

(86) PCT No.: PCT/GB2005/004996  
§ 371 (c)(1),  
(2), (4) Date: Mar. 24, 2008

(87) PCT Pub. No.: WO2006/067454  
PCT Pub. Date: Jun. 29, 2006

(65) Prior Publication Data  
US 2008/0261200 A1   Oct. 23, 2008

(30) Foreign Application Priority Data

Dec. 23, 2004   (GB) ................... 0428255.4

(51) Int. Cl.  
*C12Q 1/70* (2006.01)  
*C12Q 1/68* (2006.01)  
*C12P 19/34* (2006.01)

(52) U.S. Cl. ............... 435/5; 435/6; 435/91.1; 435/91.2

(58) Field of Classification Search ............. 435/6, 91.1, 435/91.2, 5  
See application file for complete search history.

(56) References Cited

U.S. PATENT DOCUMENTS 5,658,733 A   8/1997   Cockerill, III et al.  
(Continued)

FOREIGN PATENT DOCUMENTS

EP   0332435   3/1989  
(Continued)

OTHER PUBLICATIONS

Cheng, A.F.B. et al., "Multiplex PCR amplimer conformation analysis for rapid detection of gyrA mutations in fluoroquinolone-resistant mycobacterium tuberculosis clinical isolates", Antimicrobial Agents and Chemotherapy, vol. 48, No. 2, pp. 596-601, (2004).

(Continued)

*Primary Examiner* — Kenneth R. Horlick  
(74) *Attorney, Agent, or Firm* — Evan Law Group LLC

(57) ABSTRACT

A method for detecting a mutation in a target nucleic acid sequence in a sample, the target nucleic acid sequence comprising a first DNA strand and optionally the complementary strand thereof, said method comprising: (a) adding a detection primer to the nucleic acid, wherein the detection primer binds to the first DNA strand at a DNA sequence that comprises the mutation site; (b) extending the detection primer to form second DNA strands that are complementary to the first DNA strand; (c) adding an amplification primer to the nucleic acid, wherein the amplification primer binds to the second DNA strand and/or to the complementary strand, at a position away from the mutation site; (d) extending the amplification primer to form third DNA strands that are complementary to the second DNA strands, and/or additional copies of the first DNA strand; (e) annealing the DNA strands by complementary base pairing, to form nucleic acid duplexes, wherein if the two strands of the duplex have a mismatched residue at the mutation site, the duplex is a heteroduplex, and wherein if the two strands of the duplex do not have a mismatched residue at the mutation site, the duplex is a homoduplex; and (f) detecting the presence of heteroduplexes and/or homoduplexes.

37 Claims, 6 Drawing Sheets

U.S. PATENT DOCUMENTS

| | | |
|---|---|---|
| 6,586,181 B1 | 7/2003 | Fox et al. |
| 2003/0235855 A1 | 12/2003 | Cabral |
| 2004/0038283 A1* | 2/2004 | Brenner .......................... 435/6 |

FOREIGN PATENT DOCUMENTS

| | | |
|---|---|---|
| WO | WO 90/13668 | 11/1990 |
| WO | WO 95/01453 | 1/1995 |
| WO | WO 98/50585 | 11/1998 |
| WO | WO 02/18641 | 3/2002 |
| WO | WO 02/44335 | 6/2002 |
| WO | WO 03/14398 | 2/2003 |

OTHER PUBLICATIONS

Liu, W. et al., "Denaturing high performance liquid chromatography (dHPLC) used in the detection of germline and somatic mutations", Nucleic Acids Research, vol. 26, No. 6, pp. 1396-1400, (1998).

Maiden, M.C.J. et al., "Multilocus swquence typing: a portable approach to the identification of clones within populations of pathogenic microorganisms", Proc. Natl. Acad. Science USA, vol. 95, No. 6, pp. 3140-3145, (1998).

Randall, L.P. et al., "Detection of mutations in *Salmonella enterica* gyrA, gyrB, parC and parE genes by denaturing high performance liquid chromatography (DHPLC) using standard HPLC instrumentation", Journal of Antimicrobial Chemotherapy, vol. 56, pp. 619-623, (2005).

Skopek, T.R. et al., "Analysis of sequence alterations in a defined DNA region: comparison of temperature-modulated heteroduplex analysis and denaturing gradient gel electrophoresis", Mutation Research, vol. 430, No. 1, pp. 13-21, (1999).

International Search Report dated Apr. 26, 2006 for PCT application No. PCT/GB2005/004996.

* cited by examiner

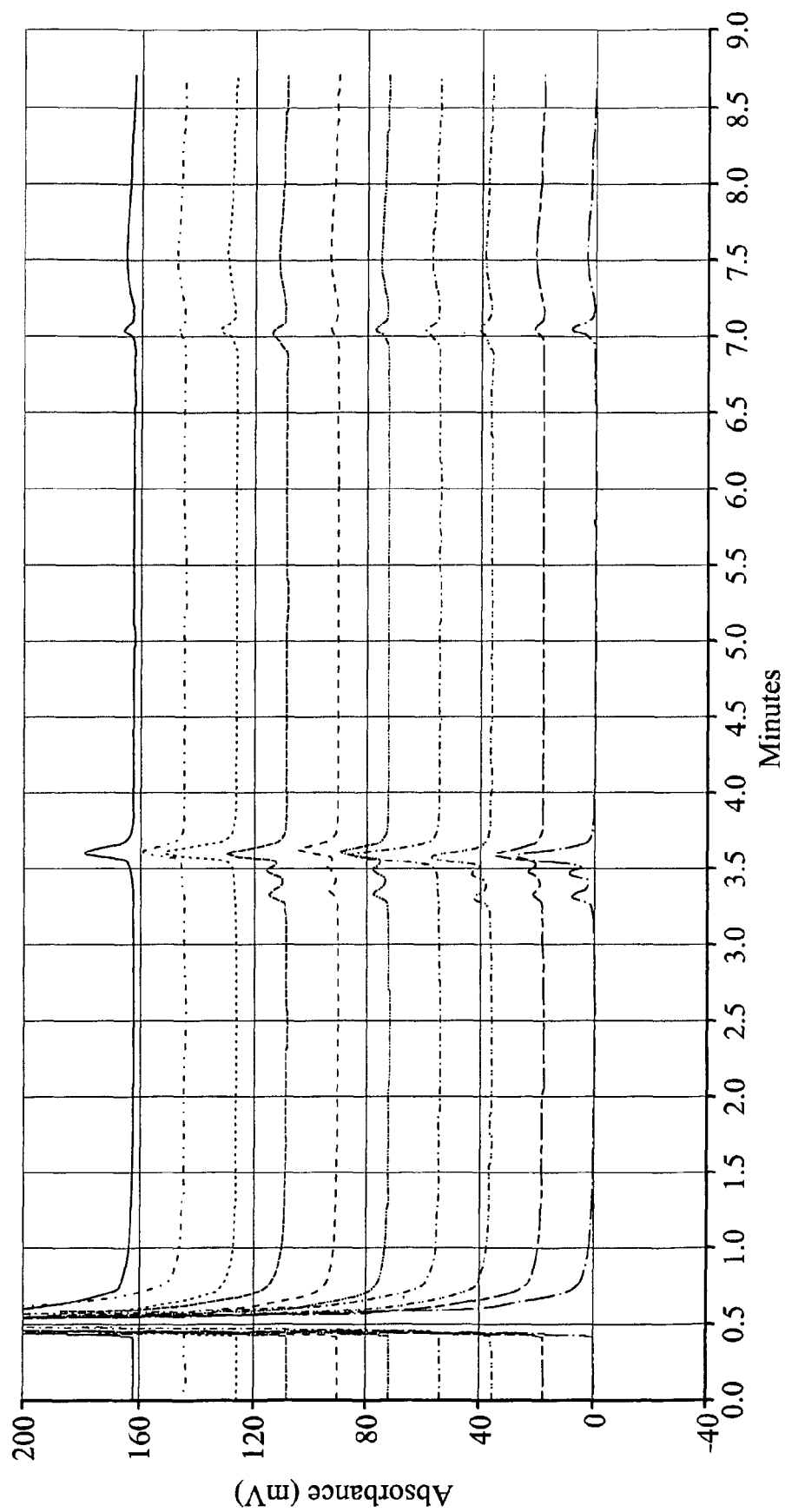
FIG. 4 (contd.)

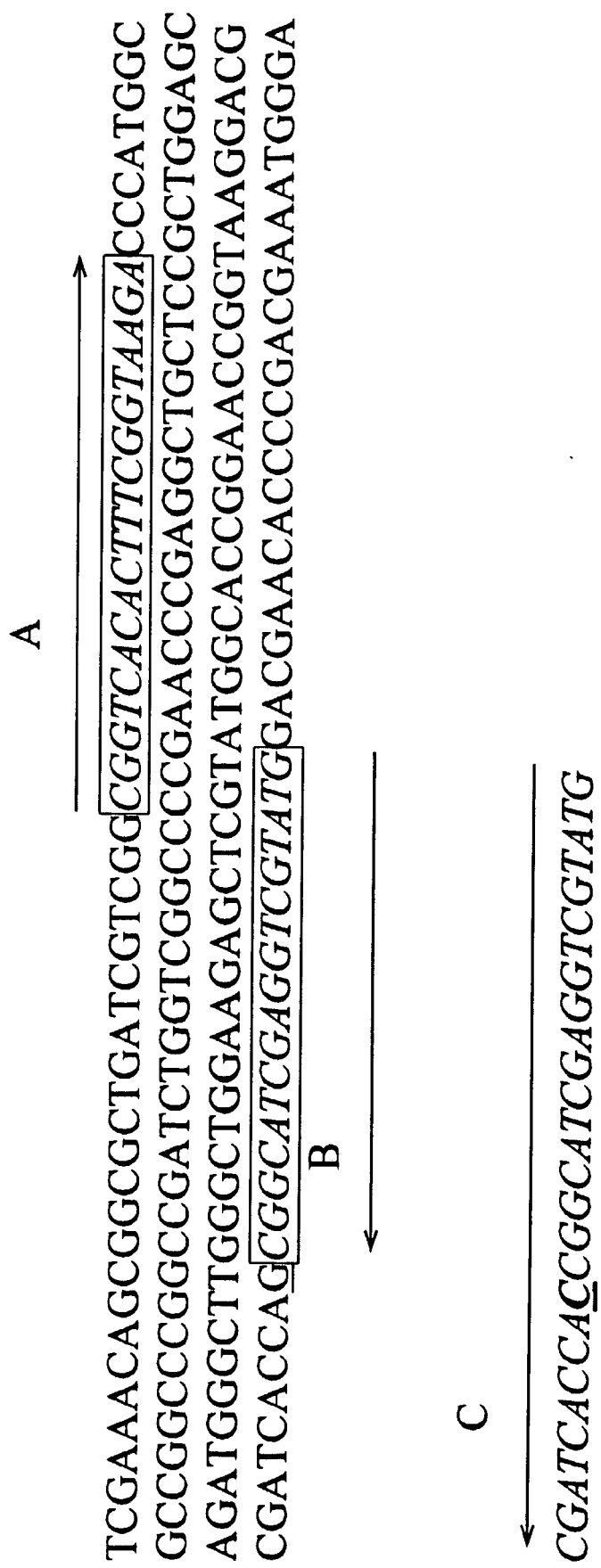

SEQUENCE LISTING

<160> NUMBER OF SEQ ID NOS: 36

<210> SEQ ID NO 1
<211> LENGTH: 2224
<212> TYPE: DNA
<213> ORGANISM: M. Tuberculosis

<400> SEQUENCE: 1

```
gtgcccgagc aacacccacc cattacagaa accaccaccg gagccgctag caacggctgt    60
cccgtcgtgg gtcatatgaa ataccccgtc gagggcggcg gaaaccagga ctggtggccc   120
aaccggctca atctgaaggt actgcaccaa aacccggccg tcgctgaccc gatgggtgcg   180
gcgttcgact atgccgcgga ggtcgcgacc atcgacgttg acgccctgac gcgggacatc   240
gaggaagtga tgaccacctc gcagccgtgg tggcccgccc actacggcca ctacgggccg   300
ctgtttatcc ggatggcgtg gcacgctgcc ggcacctacc gcatccacga cggccgcggc   360
ggcgccgggg cggcatgca gcggttcgcg ccgcttaaca gctggcccga caacgccagc   420
ttggacaagg gcgccggct gctgtggccg gtcaagaaga agtacggcaa gaagctctca   480
tgggcggacc tgattgtttt cgccggcaac tgcgcgctgg aatcgatggg cttcaagacg   540
ttcgggttcg gcttcggccg ggtcgaccag tgggagcccg atgaggtcta ttggggcaag   600
gaagccacct ggctcggcga tgagcgttac agcggtaagc gggatctgga gaacccgctg   660
gccgcggtgc agatggggct gatctacgtg aacccggagg ggccgaacgg caacccggac   720
cccatggccg cggcggtcga cattcgcgag acgtttcggc gcatggccat gaacgacgtc   780
gaaacagcgg cgctgatcgt cggcggtcac actttcggta agacccatgg cgccggcccg   840
gccgatctgg tcggcccccga acccgaggct gctccgctgg agcagatggg cttgggctgg   900
aagagctcgt atggcaccgg aaccggtaag gacgcgatca ccagcggcat cgaggtcgta   960
tggacgaaca ccccgacgaa atgggacaac agtttcctcg agatcctgta cggctacgag  1020
tgggagctga cgaagagccc tgctggcgct tggcaataca ccgccaagga cggcgccggt  1080
gccggcacca tccggacccc gttcggcggg ccagggcgct ccccgacgat gctggccact  1140
gacctctcgc tgcgggtgga tccgatctat gagcggatca cgcgtcgctg gctggaacac  1200
cccgaggaat tggccgacga gttcgccaag gcctggtaca agctgatcca ccagacatg  1260
ggtcccgttg cgagatacct tgggccgctg gtccccaagc agaccctgct gtggcaggat  1320
ccggtccctg cggtcagcca cgacctcgtc ggcgaagccg agattgccag ccttaagagc  1380
cagatccggg catcgggatt gactgtctca cagctagttt cgaccgcatg ggcggcggcg  1440
tcgtcgttcc gtggtagcga caagcgcggc ggcgccaacg gtggtcgcat ccgcctgcag  1500
```

-continued ccacaagtcg ggtgggaggt caacgacccc gacggggatc tgcgcaaggt cattcgcacc 1560
ctggaagaga tccaggagtc attcaactcc gcggcgccgg ggaacatcaa agtgtccttc 1620
gccgacctcg tcgtgctcgg tggctgtgcc gccatagaga aagcagcaaa ggcggctggc 1680
cacaacatca cggtgccctt caccccgggc cgcacggatg cgtcgcagga acaaaccgac 1740
gtggaatcct ttgccgtgct ggagcccaag gcagatggct tccgaaacta cctcggaaag 1800
ggcaacccgt tgccggccga gtacatgctg ctcgacaagg cgaacctgct tacgctcagt 1860
gcccctgaga tgacggtgct ggtaggtggc ctgcgcgtcc tcggcgcaaa ctacaagcgc 1920
ttaccgctgg gcgtgttcac cgaggcctcc gagtcactga ccaacgactt cttcgtgaac 1980
ctgctcgaca tgggtatcac ctgggagccc tcgccagcag atgacgggac ctaccagggc 2040
aaggatggca gtggcaaggt gaagtggacc ggcagccgcg tggacctggt cttcgggtcc 2100
aactcggagt tgcgggcgct tgtcgaggtc tatggcgccg atgacgcgca gccgaagttc 2160
gtgcaggact tcgtcgctgc ctgggacaag gtgatgaacc tcgacaggtt cgacgtgcgc 2220
tgat 2224

<210> SEQ ID NO 2
<211> LENGTH: 28
<212> TYPE: DNA
<213> ORGANISM: M. tuberculosis

<400> SEQUENCE: 2
cgatcaccag cggcatcgag gtcgtatg 28

<210> SEQ ID NO 3
<211> LENGTH: 28
<212> TYPE: DNA
<213> ORGANISM: Artificial sequence
<220> FEATURE:
<223> OTHER INFORMATION: wild type detection primer

<400> SEQUENCE: 3
catacgacct cgatgccgct ggtgatcg 28

<210> SEQ ID NO 4
<211> LENGTH: 28
<212> TYPE: DNA
<213> ORGANISM: Artificial sequence
<220> FEATURE:
<223> OTHER INFORMATION: mutant detection primer

<400> SEQUENCE: 4
catacgacct cgatgccggt ggtgatcg 28

<210> SEQ ID NO 5
<211> LENGTH: 2223
<212> TYPE: DNA
<213> ORGANISM: M. tuberculosis

<400> SEQUENCE: 5
gtgcccgagc aacacccacc cattacagaa accaccaccg gagccgctag caacggctgt 60
cccgtcgtgg gtcatatgaa ataccccgtc gagggcggcg gaaaccagga ctggtggccc 120
aaccggctca atctgaaggt actgcaccaa aacccggccg tcgctgaccc gatgggtgcg 180
gcgttcgact atgccgcgga ggtcgcgacc atcgacgttg acgccctgac gcgggacatc 240
gaggaagtga tgaccacctc gcagccgtgg tggcccgccg actacggcca ctacgggccg 300
ctgtttatcc ggatggcgtg gcacgctgcc ggcacctacc gcatccacga cggccgcggc 360

```
ggcgccgggg gcggcatgca gcggttcgcg ccgcttaaca gctggcccga caacgccagc    420
ttggacaagg cgcgccggct gctgtggccg gtcaagaaga agtacggcaa gaagctctca    480
tgggcggacc tgattgtttt cgccggcaac tgcgcgctgg aatcgatggg cttcaagacg    540
ttcgggttcg gcttcggccg ggtcgaccag tgggagcccg atgaggtcta ttggggcaag    600
gaagccacct ggctcggcga tgagcgttac agcggtaagc gggatctgga gaacccgctg    660
gccgcggtgc agatggggct gatctacgtg aacccggagg ggccgaacgg caaccccgac    720
cccatggccg cggcggtcga cattcgcgag acgtttcggc gcatggccat gaacgacgtc    780
gaaacagcgg cgctgatcgt cggcggtcac actttcggta agacccatgg cgccggcccg    840
gccgatctgg tcggccccga acccgaggct gctccgctgg agcagatggg cttgggctgg    900
aagagctcgt atggcaccgg aaccggtaag gacgcgatca ccaccggcat cgaggtcgta    960
tggacgaaca ccccgacgaa atgggacaac agtttcctcg agatcctgta cggctacgag   1020
tgggagctga cgaagagccc tgctggcgct tggcaataca ccgccaagga cggcgccggt   1080
gccggcacca tcccggaccc gttcggcggg ccagggcgct cccgacgat  gctggccact   1140 gacctctcgc tgcgggtgga tccgatctat gagcggatca cgcgtcgctg gctgaacac    1200 cccgaggaat tggccgacga gttcgccaag gcctggtaca agctgatcca ccgagacatg   1260
ggtcccgttg cgagatacct tgggccgctg gtccccaagc agaccctgct gtggcaggat   1320
ccggtccctg cggtcagcca cgacctcgtc ggcgaagccg agattgccag ccttaagagc   1380
cagatcctgg catcgggatt gactgtctca cagctagttt cgaccgcatg gcggcggcg    1440 tcgtcgttcc gtggtagcga caagcgcggc ggcgccaacg gtggtcgcat ccgcctgcag   1500
ccacaagtcg ggtgggaggt caacgacccc gacgggatc  tgcgcaaggt cattcgcacc   1560
ctggaagaga tccaggagtc attcaactcc gcggcgccgg ggaacatcaa agtgtccttc   1620
gccgacctcg tcgtgctcgg tggctgtgcc gccatagaga aagcagcaaa ggcggctggc   1680
cacaacatca cggtgccctt cacccccggc cgcacggatg cgtcgcagga acaaaccgac   1740
gtggaatcct ttgccgtgct ggagcccaag gcagatggct tccgaaacta cctcggaaag   1800 ggcaaccccgt tgccggccga gtacatgctg ctcgacaagg cgaacctgct tacgctcagt   1860 gccccctgaga tgacggtgct ggtaggtggc ctgcgcgtcc tcggcgcaaa ctacaagcgc   1920
ttaccgctgg gcgtgttcac cgaggcctcc gagtcactga ccaacgactt cttcgtgaac   1980
ctgctcgaca tgggtatcac ctgggagccc tcgccagcag atgacgggac ctaccagggc   2040
aaggatggca gtggcaaggt gaagtggacc ggcagccgcg tggacctggt cttcgggtcc   2100
aactcggagt tgcgggcgct tgtcgaggtc tatggcgccg atgacgcgca gccgaagttc   2160
gtgcaggact tcgtcgctgc ctgggacaag gtgatgaacc tcgacaggtt cgacgtgcgc   2220
tga                                                                2223
```

<210> SEQ ID NO 6
<211> LENGTH: 28
<212> TYPE: DNA
<213> ORGANISM: M. tuberculosis

<400> SEQUENCE: 6
cgatcaccac cggcatcgag gtcgtatg                                       28

<210> SEQ ID NO 7
<211> LENGTH: 20
<212> TYPE: DNA
<213> ORGANISM: Artificial sequence
<220> FEATURE:

<223> OTHER INFORMATION: forward amplification primer

<400> SEQUENCE: 7
cggtcacact ttcggtaaga                                              20

<210> SEQ ID NO 8
<211> LENGTH: 18
<212> TYPE: DNA
<213> ORGANISM: Artificial sequence
<220> FEATURE:
<223> OTHER INFORMATION: reverse amplification primer

<400> SEQUENCE: 8
catacgacct cgatgccg                                                18

<210> SEQ ID NO 9
<211> LENGTH: 191
<212> TYPE: DNA
<213> ORGANISM: Bacillus

<400> SEQUENCE: 9
gttgcggatt taaaagtcat tggtgataca gatcaaacgg gaacgataac tcgatttaaa    60
ccagatccag aaattttttca ggaaacaaca gtatacgaat ttgatacact agcaactcgt  120
atgcgtgaat tagcattttt aaatcgtaat attaaactga cgattgaaga taaacgtgaa  180
cataagcaaa a                                                       191

<210> SEQ ID NO 10
<211> LENGTH: 20
<212> TYPE: DNA
<213> ORGANISM: artificial sequence
<220> FEATURE:
<223> OTHER INFORMATION: primer

<400> SEQUENCE: 10
gttgcggatt taaaagtcat                                              20

<210> SEQ ID NO 11
<211> LENGTH: 17
<212> TYPE: DNA
<213> ORGANISM: artificial sequence
<220> FEATURE:
<223> OTHER INFORMATION: primer

<400> SEQUENCE: 11
ttttgcttat gttcacg                                                 17

<210> SEQ ID NO 12
<211> LENGTH: 23
<212> TYPE: DNA
<213> ORGANISM: artificial sequence
<220> FEATURE:
<223> OTHER INFORMATION: primer

<400> SEQUENCE: 12
aaagtcatcg gtgatacaga taa                                          23

<210> SEQ ID NO 13
<211> LENGTH: 27
<212> TYPE: DNA
<213> ORGANISM: artificial sequence
<220> FEATURE:
<223> OTHER INFORMATION: primer

<400> SEQUENCE: 13

-continued aaagtcattg gtgacaccga tcaaaca    27

<210> SEQ ID NO 14
<211> LENGTH: 226
<212> TYPE: DNA
<213> ORGANISM: Bacillus

<400> SEQUENCE: 14
tttttaaatc gtaatattaa actgacgatt gaagataaac gtgaacataa gcaaaaaaaa    60
gaattccatt atgaaggtgg aattaaatca tatgttgagc atttaaaccg ctcaaaacaa    120
ccaatccatg aagagcctgt atatgtagaa ggatcaaaag atggtattca agttgaagtt    180
tccttacagt ataacgaagg atatacaaat aatatttact cattta    226

<210> SEQ ID NO 15
<211> LENGTH: 21
<212> TYPE: DNA
<213> ORGANISM: artificial sequence
<220> FEATURE:
<223> OTHER INFORMATION: primer

<400> SEQUENCE: 15
tttttaaatc gtaatattaa a    21

<210> SEQ ID NO 16
<211> LENGTH: 22
<212> TYPE: DNA
<213> ORGANISM: artificial sequence
<220> FEATURE:
<223> OTHER INFORMATION: primer

<400> SEQUENCE: 16
taaatgagta aatattattt gt    22

<210> SEQ ID NO 17
<211> LENGTH: 23
<212> TYPE: DNA
<213> ORGANISM: artificial sequence
<220> FEATURE:
<223> OTHER INFORMATION: primer

<400> SEQUENCE: 17
gtaatattaa actgacgatt gaa    23

<210> SEQ ID NO 18
<211> LENGTH: 310
<212> TYPE: DNA
<213> ORGANISM: Bacillus

<400> SEQUENCE: 18
tcatttcctt acgctacttt ttattctttt cataccagag cgtttaaaga catgaattaa    60
gcttttcttt aattcttcat atgtcatctc tgcacaaggc ttccttgcta ttataacaaa    120
atcttttcca gaatctatct catctttttaa ttctgtgatc gactggcgaa tcatacgttt    180
aattcggtta cgcactactg catttcctat cttcttgctg acagaaaggc caatacgaaa    240
gtttggctgc tcttctttat ctagttgata gacaacaaat tgacgattcg cattcgattt    300
tcctttttga    310

<210> SEQ ID NO 19
<211> LENGTH: 20
<212> TYPE: DNA
<213> ORGANISM: artificial sequence
<220> FEATURE:

```
<223> OTHER INFORMATION: primer

<400> SEQUENCE: 19
tcatttcctt acgctactttt                                                  20

<210> SEQ ID NO 20
<211> LENGTH: 21
<212> TYPE: DNA
<213> ORGANISM: artificial sequence
<220> FEATURE:
<223> OTHER INFORMATION: primer

<400> SEQUENCE: 20
tcaaaaagga aaatcgaatg c                                                 21

<210> SEQ ID NO 21
<211> LENGTH: 25
<212> TYPE: DNA
<213> ORGANISM: artificial sequence
<220> FEATURE:
<223> OTHER INFORMATION: primer

<400> SEQUENCE: 21
tcatttcctt acgctactttt ttatt                                            25

<210> SEQ ID NO 22
<211> LENGTH: 175
<212> TYPE: DNA
<213> ORGANISM: Bacillus

<400> SEQUENCE: 22
ccaccaacag tagaaaatgc caagagctta cttgtgtctc gtttcttcga tccaaagcgc       60
tatgatttag caaatgtagg tcgctacaag atcaacaaga agttacacat taaaaacaga     120
ttgtttaacc aacgtttagc tgaaacatta gtagatccag aaactggtga aattt          175

<210> SEQ ID NO 23
<211> LENGTH: 20
<212> TYPE: DNA
<213> ORGANISM: artificial sequence
<220> FEATURE:
<223> OTHER INFORMATION: primer

<400> SEQUENCE: 23
ccaccaacag tagaaaatgc                                                   20

<210> SEQ ID NO 24
<211> LENGTH: 22
<212> TYPE: DNA
<213> ORGANISM: artificial sequence
<220> FEATURE:
<223> OTHER INFORMATION: primer

<400> SEQUENCE: 24
aaatttcacc agtttctgga tc                                                22

<210> SEQ ID NO 25
<211> LENGTH: 23
<212> TYPE: DNA
<213> ORGANISM: artificial sequence
<220> FEATURE:
<223> OTHER INFORMATION: primer

<400> SEQUENCE: 25
aacagtagaa aatgccaaga gct                                               23
```

```
<210> SEQ ID NO 26
<211> LENGTH: 16
<212> TYPE: PRT
<213> ORGANISM: S. enterica

<400> SEQUENCE: 26

His Pro His Gly Asp Ser Ala Val Tyr Asp Thr Ile Val Arg Met Ala
1               5                   10                  15

<210> SEQ ID NO 27
<211> LENGTH: 96
<212> TYPE: DNA
<213> ORGANISM: S. enterica

<400> SEQUENCE: 27
catccccacg gcgattccgc agtgtatgac accatcgttc gtatggcggt agggggtgccg      60 ctaaggcgtc acatactgtg gtagcaagca taccgc                                 96

<210> SEQ ID NO 28
<211> LENGTH: 19
<212> TYPE: DNA
<213> ORGANISM: artificial sequence
<220> FEATURE:
<223> OTHER INFORMATION: probe

<400> SEQUENCE: 28
cgtcacatac tgtggtagc                                                    19

<210> SEQ ID NO 29
<211> LENGTH: 19
<212> TYPE: DNA
<213> ORGANISM: artificial sequence
<220> FEATURE:
<223> OTHER INFORMATION: probe

<400> SEQUENCE: 29
gtcacatacc gtggtagca                                                    19

<210> SEQ ID NO 30
<211> LENGTH: 19
<212> TYPE: DNA
<213> ORGANISM: artificial sequence
<220> FEATURE:
<223> OTHER INFORMATION: probe

<400> SEQUENCE: 30
gtcacatacg gtggtagca                                                    19

<210> SEQ ID NO 31
<211> LENGTH: 20
<212> TYPE: DNA
<213> ORGANISM: artificial sequence
<220> FEATURE:
<223> OTHER INFORMATION: probe

<400> SEQUENCE: 31
cgtcacataa tgtggtagca                                                   20

<210> SEQ ID NO 32
<211> LENGTH: 20
<212> TYPE: DNA
<213> ORGANISM: artificial sequence
<220> FEATURE:
<223> OTHER INFORMATION: probe

<400> SEQUENCE: 32
```

```
cgtcacatat tgtggtagca                                                20

<210> SEQ ID NO 33
<211> LENGTH: 18
<212> TYPE: DNA
<213> ORGANISM: artificial sequence
<220> FEATURE:
<223> OTHER INFORMATION: probe

<400> SEQUENCE: 33
gtgccgctaa ggcgtcac                                                  18

<210> SEQ ID NO 34
<211> LENGTH: 18
<212> TYPE: DNA
<213> ORGANISM: artificial sequence
<220> FEATURE:
<223> OTHER INFORMATION: probe

<400> SEQUENCE: 34
gtgccgctaa agcgtcac                                                  18

<210> SEQ ID NO 35
<211> LENGTH: 18
<212> TYPE: DNA
<213> ORGANISM: artificial sequence
<220> FEATURE:
<223> OTHER INFORMATION: probe

<400> SEQUENCE: 35
gtgccgctaa tgcgtcac                                                  18

<210> SEQ ID NO 36
<211> LENGTH: 18
<212> TYPE: DNA
<213> ORGANISM: artificial sequence
<220> FEATURE:
<223> OTHER INFORMATION: probe

<400> SEQUENCE: 36 gtagggtga cgctaagg                                                   18
```

DETECTION OF NUCLEIC ACID MUTATIONS BY DETECTING THE PRESENCE OF HETERODUPLEXES

The present invention relates to a method for detecting one or more known nucleic acid mutations in a nucleic acid sequence, and to reagents and kits therefor.

Nucleic acid sequence mutations (eg. polymorphisms) may be detected using PCR amplification followed by DNA sequence analysis. Nucleic acid sequences can be determined by pyro-sequencing using commercially available sequencing equipment, however, a disadvantage of this method is that labelled (in particular, fluorescently labelled) primers are required. Hence, various alternative methods for sequence analysis of nucleic acid mutations have been employed in the art.

Known methods for detection of nucleic acid sequence mutations fall into two categories—(1) scanning methods for discovering previously unknown mutations; and (2) diagnostic methods for detecting known mutations.

Known diagnostic methods for detection of known mutations include mass spectrometry, RFLP (restriction fragment length polymorphism), PFGE (pulsed-field gel electrophoresis), FAFLP (fluorescent amplified fragment length polymorphism), Rnase A cleavage, ASOs (allele specific oligonucleotides), 5' nuclease assay (real-time PCR "TaqMan" assay), primer extension (including SnaPshot and SNP-IT technologies), and Molecular Beacons (real-time PCR).

By way of example, one technique for detecting known sequence polymorphisms is melting curve analysis. Different mutations in a given sequence generate a characteristic melt curve using real-time PCR equipment such as a LightCycler (Roche). Mutations in PCR products can also be identified using fluorescent probes.

A further method for sequence analysis is reverse hybridisation. A labelled PCR product is generated that includes the mutation of interest, and this is used to interrogate a series of probes immobilised on a solid support. By way of example, a system for detecting mutations in the *Mycobacterium tuberculosis* rpoB gene is commercially available (INNO-LiPA Rif.TB, Innogenetics, Gent, Belgium). This technique is limited, however, by its relatively high cost.

Another method for sequence analysis is agarose gel electrophoresis, which requires mutation specific amplification. The size of the resultant PCR product in a gel indicates the presence of a given mutation.

Scanning methods for discovering unknown sequence mutations include SSCP (single strand conformation polymorphism analysis), in which an amplified PCR product is denatured, and the resultant single stranded DNA is passed down an acrylamide gel—a typical migration pattern being seen if a polymorphism is present.

Denaturing High Performance Liquid Chromatography (dHPLC) has also been used in the art for discovering previously unknown differences (eg. mutations) between PCR amplification products. Detection of these sequence differences relies upon detection of the presence or absence of DNA heteroduplexes.

In more detail, this known method involves mixing the products of two PCR reactions (for example a wild type reference sample, "Sample A", and a sample of interest, "Sample B", which may contain a mutation, or may also be wild type), and heating the mixed PCR products to 94° C. for 5 minutes. As the PCR products are cooled very gradually to 25° C., the separated strands will anneal to form duplexes. If "Sample B" does not contain the mutation (ie. it is wild type), then only homoduplexes will form—ie. duplexes corresponding to the wild type nucleic acid in the 2 samples. However, if "Sample B" contains a mutation then there are four possible different duplexes that may form—as illustrated in FIG. 1. Two different homoduplexes will form, corresponding to the wild type nucleic acid in "Sample A", and the mutated nucleic acid in "Sample B". In addition, two different heteroduplexes will form, each corresponding to one strand from the "Sample A" wild type nucleic acid, and one strand from the "Sample B" mutated nucleic acid. At the mutated site, the heteroduplexes will contain a mismatch.

Heteroduplexes are detected by detecting their migration pattern, which differs from that of the corresponding homoduplex. In more detail, a sample containing only homoduplexes will produce a single peak elution profile from the dHPLC column. In contrast, if heteroduplexes are present, a three-peak profile will be seen.

Hence, this technique is used in the art for discovering previously unknown mutations in nucleic acid sequences—using a wild type reference sample, heteroduplexes will form if a mutation is present in the sample of interest, whereas the absence of heteroduplexes indicates that the sample of interest is wild type.

A variation of this technique can also be used for detection of a specific, known mutation of interest, in which case the reference sample PCR products contain the known mutation. Heteroduplexes will be detected if the sample of interest contains only wild type nucleic acid, but no heteroduplexes will be detected if the sample of interest contains the specific mutation that is present in the reference sample.

A disadvantage of this known method is that it is labour intensive, as it requires mixing of the PCR products of the sample of interest with the PCR products of a second, "reference" sample prior to heteroduplex formation. Hence, this method can only be used for detecting a known mutation in a sample of interest if a reference sample is available that also contains that specific known mutation. This known method also has limitations where multiple mutations are to be detected.

There is, therefore, a need in the art for an alternative and/or improved method for detecting specific mutations in nucleic acid sequences, that overcomes or at least ameliorates one or more of the problems associated with the prior art methods.

A method for detecting a mutation in a target nucleic acid sequence in a sample, the target nucleic acid sequence comprising a first DNA strand and optionally the complementary strand thereof, said method comprising: (a) adding a detection primer to the nucleic acid, wherein the detection primer binds to the first DNA strand at a DNA sequence that comprises the mutation site; (b) extending the detection primer to form second DNA strands that are complementary to the first DNA strand; (c) adding an amplification primer to the nucleic acid, wherein the amplification primer binds to the second DNA strand and/or to the complementary strand, at a position away from the mutation site; (d) extending the amplification primer to form third DNA strands that are complementary to the second DNA strands, and/ or additional copies of the first DNA strand; (e) annealing the DNA strands by complementary base pairing, to form nucleic acid duplexes, wherein if the two strands of the duplex have a mismatched residue at the mutation site, the duplex is a heteroduplex, and. wherein if the two strands of the duplex do not have a mismatched residue at the mutation site, the duplex is a homoduplex; and (f) detecting the presence of heteroduplexes and/or homoduplexes.

Thus, the present method enables detection of a known nucleic acid sequence mutation (eg. a polymorphism), by obtaining heteroduplexes and/or homoduplexes during PCR without the need for a reference sample.

Steps a) to d) may be carried out sequentially or substantially simultaneously. Alternatively, just steps a) and c) may be carried out substantially simultaneously, followed by steps b) and d). It is also an option for steps b) and d) to be carried out substantially simultaneously.

A sample may be for instance, a food, sewerage or clinical sample.

A mutation (eg. a polymorphism) detectable by the present invention may be a nucleic acid deletion, insertion, or substitution. In one embodiment, multiple mutations may be detected, selected from the group consisting of nucleic acid deletions, insertions and substitutions. The mutations may be in the same or different target nucleic acids.

Thus, a mutation site in a target nucleic acid is a site that may or may not contain a nucleic acid deletion, insertion or substitution. If the deletion, insertion or substitution is present at the mutation site, then the target nucleic acid is a "mutant" target nucleic acid. In the other hand, if the polymorphism site does not contain the nucleic acid deletion, insertion or substitution, then the target nucleic acid is a "wild type" target nucleic acid. In this regard, the terms "mutation site" and "polymorphism site" have the same meaning, and they are intended to be interchangeable.

The detection primer is so named because it binds to a mutation site in the target nucleic acid, and enables detection of whether or not a nucleic acid mutation, such as a deletion, insertion or substitution, is present at that mutation site. The detection primer is capable of binding to the target nucleic acid regardless of whether or not there is a mutation at the mutation site.

The detection primer may be a "wild type detection primer". A wild type detection primer is so named because it comprises a nucleic acid residue that is complementary to a wild type residue at the mutation site. When a wild type detection primer is used in the method, the presence of heteroduplexes indicates that the sample contains target nucleic acid having a mutant residue at the mutation site—ie. mutant target nucleic acid.

Alternatively, the detection primer may be a "mutant detection primer". A mutant detection primer is so named because it comprises a nucleic acid residue that is complementary to a mutant residue at the mutation site. When a mutant detection primer is used in the method, the presence of heteroduplexes indicates that the sample contains target nucleic acid having a wild type residue at the mutation site—ie. wild type target nucleic acid.

The amplification primer binds to the second DNA strand, and/or to the complementary DNA strand, at a position away from the mutation site. The amplification primer may be a forward or reverse primer, depending on whether the selected detection primer is a forward or reverse primer. By "a position away from the mutation site" we mean that the amplification primer does not bind to the mutation site, and preferably binds to a site that is separated from the mutation site by at least 5, preferably at least 10, more preferably at least 20, most preferably at least 50 residues.

A forward primer is a primer that binds to the non-coding (anti-sense) strand of the target nucleic acid and a reverse primer is a primer that binds to the coding (sense) strand of the target nucleic acid. In this regard, the first DNA strand may be either the non-coding (anti-sense) DNA strand, or the coding, (sense) DNA strand of the target nucleic acid. Likewise, the complementary strand may be either the non-coding (anti-sense) DNA strand, or the coding (sense) DNA strand of the target nucleic acid—depending on whether the first DNA strand is the coding or the non-coding strand.

In more detail, in one embodiment, the detection primer may be a forward primer, in which case the amplification primer is a reverse primer. Optionally, the method may comprise adding a third primer, which may be a forward amplification primer that binds to the first DNA strand or to the third DNA strand, at a position away from the mutation site. Hence, in this embodiment, the method may comprise adding two different types of forward primer. Preferably, the forward amplification primer has a lower annealing temperature than the detection primer, and more preferably, the forward amplification primer is shorter than the detection primer.

In an alternative embodiment, the detection primer may be a reverse primer, in which case the amplification primer is a forward primer. Optionally, the method may comprises adding a third primer, which may be a reverse amplification primer that binds to the first DNA strand or to the third DNA strand, at a position away from the mutation site. Hence, in this embodiment, the method may comprise adding two different types of reverse primer. Preferably, the reverse amplification primer has a lower annealing temperature than the detection primer, and more preferably, the reverse amplification primer is shorter than the detection primer.

In one embodiment, the method uses a detection primer that is at least 15 nucleotides long. It is preferred that the detection primer is at least 20 nucleic acids long, more preferably at least 25 nucleic acids long, most preferably about 25 to 30 nucleic acids long.

The amplification primer(s) is typically 1 to 50 nucleotides long, preferably 10 to 40 nucleotides long, more preferably 15 to 25 nucleotides long. It is generally advantageous to use short primers, as this enables faster binding to target nucleic acid. In one embodiment, the amplification primer(s) is shorter than the detection primer.

The amplification primers and the detection primer of the present invention are designed to bind to the target nucleic acid sequence based on the selection of desired parameters, using conventional software, such as Primer Express (Applied Biosystems). The primers are preferably screened to minimise self-complementarity and primer-to-primer binding.

It is preferred that the primer binding conditions are such that a high level of specificity is provided. The melting temperature (Tm) of the amplification primer(s) and detection primer may be 50° C. or higher, preferably about 60° C. It is preferred that the detection primer has a higher melting temperature than the amplification primer(s).

The primers are preferably extended in steps b) and d) from their 3' ends—ie. in the 5' to 3' direction. In a preferred embodiment, the extending step a) is carried out at a high annealing temperature, at which the detection primer can bind to the target nucleic acid, but the amplification primer(s) can preferably not bind to the target nucleic acid. Following several rounds of extending at the high annealing temperature, using the detection primer, extending step c) is preferably carried out at a lower annealing temperature, at which the amplification primer(s) can bind to the target nucleic acid.

The extending steps b) and d) may be carried out by any suitable method, and in a preferred embodiment the extending is carried out by PCR. The amplification primer(s) and the detection primer are extended using a DNA polymerase and dNTPs, resulting in generation of multiple copies of the first DNA strand and its complementary strand, and the second and third DNA strands.

The second DNA strand will incorporate the sequence of the detection primer—ie. any sequence difference between the detection primer and the target nucleic acid at the mutation site will be incorporated into the second DNA strand.

Hence, if the target nucleic acid is wild type at the mutation site in the first DNA strand, but the detection primer is mutant at the mutation site, then second strands will be generated in extending step b) that are mutant at the mutation site. Hence, although the starting template material may be pure wild type target nucleic acid, the present method enables generation of some mutant nucleic acid strands. These generated mutant strands may combine with the wild type strands to generate a heteroduplex, which may be detected.

Alternatively, if the target nucleic acid is mutant at the mutation site in the first DNA strand, but the detection primer is wild type at the mutation site, then second Strands will be generated in step b) that are wild type at the mutation site. Hence, although the starting template material may be pure mutant target nucleic acid, the present method enables generation of some wild type nucleic acid strands. These generated wild type strands may combine with the mutant strands to generate a heteroduplex, which may be detected.

The strands may be annealed to form nucleic acid duplexes by any known method, for example, by reducing the temperature in the amplification reaction. The strands preferably anneal by complementary base-pairing. In this regard, a number of sequence mismatches are permitted. Thus, a strand that is wild type at the mutation site may anneal with a strand that is mutant at the mutation site—resulting in a mismatched residue at the mutation site, and hence a heteroduplex.

Heteroduplexes and/or homoduplexes may be detected by any known means, and in a preferred embodiment, detection is carried out by denaturing high-performance liquid chromatography (dHPLC). If heteroduplexes are present, a characteristic "3-peak" elution profile from the dHPLC column will be seen. However, if all the duplexes elute in a single peak, this indicates that no heteroduplexes are present—ie. the duplexes are all homoduplexes.

The target nucleic acid sample may be a pure sample (ie. in which the nucleic acids in the sample are all wild type or all mutant). Alternatively, the target nucleic acid sample may be a mixed sample containing both mutant and wild type nucleic acid. In order to distinguish between these two types of sample, steps a) to e) of the present method may be repeated using a different type of detection primer to that used in the first round of the method.

In more detail, in one embodiment, steps a) to e) of the method are first carried out using a wild type detection primer, and then steps a) to e) of the method are subsequently repeated using a mutant detection primer. If heteroduplexes are detected in the first and in the subsequent runs, then this indicates that the sample contains a mixture of wild type and mutant target nucleic acid.

However, if heteroduplexes are detected when the method is first carried out using a wild type detection primer, but no heteroduplexes are detected following a subsequent round of the method using a mutant detection primer, then this indicates that the sample contains only mutant target nucleic acid. Likewise, if heteroduplexes are detected when the method is first carried out using a mutant detection primer, but no heteroduplexes are detected following a subsequent round of the method with a wild type detection primer, then this indicates that the sample contains only wild type target nucleic acid.

Thus, if a first round of the method used a wild type detection primer, and heteroduplexes were detected, then in order to identify whether the sample contains only mutant target nucleic acid, or a mixture of mutant and wild type nucleic acid, steps a) to e) should be repeated using a mutant detection primer. If heteroduplexes are also detected after the subsequent round with the mutant detection primer, this would indicate that the sample contains a mixture of mutant and wild type target nucleic acid.

Alternatively, if a first round of the method used a mutant detection primer, and heteroduplexes were detected, then in order to identify whether the sample contains only wild type target nucleic acid, or a mixture of wild type and mutant nucleic acid, steps a) to e) should be repeated using a wild type detection primer. If heteroduplexes are also detected after the subsequent round with the wild type detection primer, this would indicate that the sample contains a mixture of wild type and mutant target nucleic acid.

In one embodiment, the target nucleic acid is single stranded. In one embodiment, the target nucleic acid is RNA, which is converted into cDNA prior to annealing step (a).

Where we refer to sequences having "at least 80% sequence identity" to a sequence of the present invention, this embraces sequences that have preferably at least 85% sequence identity, preferably at least 90% sequence identity, more preferably at least 95% identity, more preferably at least 98% sequence identity, most preferably at least 99% sequence identity to sequences of the present invention.

Sequences (eg. primer sequences) having at least 80% sequence identity, preferably at least 85% sequence identity, preferably at least 90% sequence identity, more preferably at least 95% identity, more preferably at least 98% sequence identity, most preferably at least 99% sequence identity to sequences of the present invention may be identified by sequence alignments using conventional software, for example the Bioedit™ package, available free online, and the Sequencher™ package, provided by Sequencher Gene Codes Corporation, 640 Avis Drive Suite 310, Ann Arbor Mich. 48108.

An alternative means for defining primer sequences that are homologous to primer sequences of the present invention is by defining the number of nucleotides that differ between the homologous sequence and the sequence of the invention. In this regard, the present invention embraces probe sequences that differ from the primer sequences of the invention by no more than 6 nucleotides, preferably by no more than 5 nucleotides, preferably by no more than 4 nucleotides, more preferably by no more than 3 nucleotides, yet more preferably by no more than 2 nucleotides, and most preferably by no more than 1 nucleotide.

In one embodiment, the method of the present invention may be used to detect mutations in a bacterial or viral nucleic acid sequence, such as a pathogenic bacterial or viral nucleic acid sequence. The mutation may confer resistance in the bacterium or virus to one or more drugs. With regard to bacterial nucleic acid sequences, the mutation may confer resistance to one or more antibiotics.

The nucleic acid sequence may be from an aerobic bacterium such as *bacillus, mycobacterium* or *neisseria* species, or may be from an anaerobic bacterium or facultative anaerobic bacterium, such as *salmonella* species.

The nucleic acid sequence may be from a Gram +ve bacterial species such as *bacillus* or *mycobacterium*, or may be from a Gram −ve species such as *salmonella* species.

The nucleic acid sequence may be from a enterobacterium, such as *salmonella* species.

Thus, the present method allows-detection of a mutation in a nucleic acid sequence of a *salmonella* species, such as *Salmonella enterica*; a *bacillus* species, such as *B. cereus* or *B. subtilis*; a *Neisseria* species such as *N. meningitides*; or a *Mycobacterium* sp. such as *Mycobacterium tuberculosis* (*M. tuberculosis*). The mutation may confer resistance to one or more antibiotics used to treat an infection, such as an *M. tuberculosis* infection —for example, rifampin or isoniazid.

The mutation may also distinguish between different bacterial species and/or strains.

With regard to *M. tuberculosis*, at least 11 genes have been reported to be involved in the development of resistance to the main anti-TB drugs. Detecting the presence of mutations that confer rifampin resistance (RIF resistance) or isoniazid resistance (INH resistance), is of importance clinically and for public health TB control.

Resistance to rifampin and isoniazid is conferred by mutations in three *M. tuberculosis* genes. RIF resistance is generally associated with single nucleotide substitutions. Mutations in the 81 bp core region of the rpoB gene (encoding the β-subunit of RNA polymerase) are known to be responsible for over 90% of RIF resistance.

Mutations in two different genes are known to be responsible for resistance to isoniazid. In more than 75% of cases, INH resistance occurs due to substitutions in the katG gene (encoding catalase-peroxidase). One of the most common substitutions in katG results in a mutation at $Ser^{315}$ of the translated polypeptide. More rarely, INH resistance is due to mutations in the inhA and ahpC genes.

Hence, the present invention enables detection of mutations in *M. tuberculosis* genes such as the rpoB, katG, inhA and ahpC genes.

By way of example, the present method may be used to detect mutant *Mycobacterium* sp. in a clinical sample. Clinical samples may include broncho-alveolar lavage specimens (BALS), induced sputa, oropharyngeal washes, blood or other body fluid samples.

Thus, in one embodiment, the present method is for detection of one or more mutations in a *Mycobacterium* sp. nucleic acid sequence, comprising the nucleic acid sequence SEQ ID NO: 1. In this regard, the *M. tuberculosis* katG gene comprises a mutation site at nucleotide residue 944 (corresponding to codon 315 in the translated polypeptide). In the wild type version of the katG gene, represented by SEQ ID NO: 1, nucleotide residue 944 is a guanine (resulting in a serine at codon 315) and in a mutant version of the katG gene, represented by SEQ ID NO: 5, nucleotide residue 944 is a cytosine, resulting in a threonine at codon 315). Hence, the present method may be used for detection of a G-C mutation at nucleotide residue 944 of the *M. tuberculosis* katG gene.

A detection primer for detecting one or more mutations in the wild type nucleic acid sequence SEQ ID NO: 1 preferably binds to a region of SEQ ID NO: 1 comprising a sequence that is at least 80% identical, preferably at least 85% identical, more preferably at least 90% identical, most preferably at least 95%, 96%, 97%, 98% or 99% identical to SEQ ID NO: 2, or to the complement thereof. In this regard, SEQ ID NO: 2 represents a 28 nucleotide sequence within SEQ ID NO: 1, and comprises residue 944 of SEQ ID NO: 1.

Likewise, a detection primer for detecting the mutant nucleic acid sequence SEQ ID NO: 5 preferably binds to a region of SEQ ID NO: 5 comprising a sequence that is at least 80% identical, preferably at least 85% identical, more preferably at least 90% identical, most preferably at least 95%, 96%, 97%, 98% or 99% identical to SEQ ID NO: 6, or to the complement thereof. In this regard, SEQ ID NO: 6 represents a 28 nucleotide sequence within SEQ ID NO: 5, and comprises residue 944 of SEQ ID NO: 5.

The detection primer may be a wild type detection primer comprising the nucleic acid sequence of SEQ ID NO: 3, or a sequence having at least 80% identity thereto, preferably at least 85%, more preferably at least 90%, most preferably at least 95%, 96%, 97%, 98% or 99% identity thereto, with the proviso that the underlined residue within SEQ ID NO: 3 is essential, and may not be substituted by any other nucleotide. Alternatively, the wild type detection primer may comprise the complement of SEQ ID NO: 3 (or a sequence having at least 80% identity thereto, preferably at least 85%, more preferably at least 90%, most preferably at least 95%, 96%, 97%, 98% or 99% identity thereto), with the proviso that the complement of the underlined residue within SEQ ID NO: 3 is essential, and may not be substituted by any other nucleotide.

Alternatively, the detection primer may be a mutant detection primer comprising the nucleic acid sequence of SEQ ID NO: 4, or a sequence having at least 80% identity thereto, preferably at least 85%, more preferably at least 90%, most preferably at least 95%, 96%, 97%, 98% or 99% identity thereto, with the proviso that the underlined residue within SEQ ID NO: 4 is essential, and may not be substituted by any other nucleotide. In an alternative embodiment, the mutant detection primer may comprise the complement of SEQ ID NO: 4 (or a sequence having at least 80% identity thereto, preferably at least 85%, more preferably at least 90%, most preferably at least 95%, 96%, 97%, 98% or 99% identity thereto), with the proviso that the complement of the underlined residue within SEQ ID NO: 4 is essential, and may not be substituted by any other nucleotide.

The present invention thus also provides a detection primer that binds to a region of SEQ ID NO: 1 comprising a sequence that is at least 80% identical, preferably at least 85% identical, more preferably at least 90% identical, most preferably at least 95%, 96%, 97%, 98% or 99% identical to SEQ ID NO: 2, or the complement thereof; or to a region of SEQ ID NO: 5 comprising a sequence that is at least 80% identical, preferably at least 85% identical, more preferably at least 90% identical, most preferably at least 95%, 96%, 97%, 98% or 99% identical to SEQ ID NO: 6, or the complement thereof.

The detection primer may be a wild type detection primer comprising the nucleic acid sequence of SEQ ID NO: 3, or a sequence having at least 80% identity thereto, preferably at least 85%, more preferably at least 90%, most preferably at least 95%, 96%, 97%, 98% or 99% identity thereto, with the proviso that the underlined residue within SEQ ID NO: 3 is essential, and may not be substituted by any other nucleotide. Alternatively, the wild type detection primer may comprise the complement of SEQ ID NO: 3 (or a sequence having at least 80% identity thereto, preferably at least 85%, more preferably at least 90%, most preferably at least 95%, 96%, 97%, 98% or 99% identity thereto), with the proviso that the complement of the underlined residue within SEQ ID NO: 3 is essential, and may not be substituted by any other nucleotide.

Alternatively, the detection primer may be a mutant detection primer comprising the nucleic acid sequence of SEQ ID NO: 4, or a sequence having at least 80% identity thereto, preferably at least 85%, more preferably at least 90%, most preferably at least 95%, 96%, 97%, 98% or 99% identity thereto, with the proviso that the underlined residue within SEQ ID NO: 4 is essential, and may not be substituted by any other nucleotide. In an alternative embodiment, the mutant detection primer may comprise the complement of SEQ ID NO: 4 (or a sequence having at least 80% identity thereto, preferably at least 85%, more preferably at least 90%, most preferably at least 95%, 96%, 97%, 98% or 99% identity thereto), with the proviso that the complement of the underlined residue within SEQ ID NO: 4 is essential, and may not be substituted by any other nucleotide.

The present invention also provides a kit for detection of a specific mutation at a mutation site in a particular target nucleic acid sequence, the kit comprising a) a detection primer that binds to a mutation site present in the first DNA strand; (b) an amplification primer that binds to a second DNA strand that is complementary to the first DNA strand, and/or to the complementary strand, at a position away from the mutation site; c) a polymerase, and d) at least one nucleotide.

The kit may be used for detecting mutations in any nucleic acid, depending on the sequence of the detection and amplification primers. Thus, in one embodiment, the kit may be for detecting mutations in a *Mycobacterium* sp. target nucleic acid sequence, such as a *M. tuberculosis* target nucleic acid sequence. In particular, the kit may be for detecting mutations in SEQ ID NO: 1, or for detecting SEQ ID NO: 5, in which case the kit may comprise a detection primer as defined above.

The nucleic acid of certain hard to distinguish bacterial species is known to differ between the species at specific polymorphic sites. Thus, the present invention enables detection of these polymorphisms, thereby distinguishing these groups of bacterial species. By way of example, the present invention enables two groups of *Bacillus* species, *B. cereus* and *B. subtilis*, to be distinguished, by detecting certain polymorphisms in the GyrA, rnpB and rpoB genes that differ between these species.

The method of the present invention may also be used for typing bacteria or viruses, such as pathogenic bacteria or viruses, for example aerobic species such as *Neisseria* (eg. *N. meningitides*). In this regard, it is known that mutations in 7 housekeeping genes are useful for distinguishing between *N. meningitides* strains (Maiden et al., *Proc Natl Acad Sci USA*. 1998 Mar. 17; 95(6):3140-5).

Another example of typing using the method of the present invention would be geno-grouping of Hepatitis C. Mixed infections exist, and treatment of the disease would be better informed with greater knowledge of the genotype (some genotypes are more resistant to treatment than others). By detecting certain specific mutations, the method of the present invention enables detection of minor genotypes.

BRIEF DESCRIPTION OF THE DRAWINGS

The present invention is discussed in more detail, by means of the Example described below, and by the accompanying Figures, in which:

FIG. 5 illustrates the location of the sequences to which forward and reverse amplification primers and a reverse detection primer bind for detection of the KatG315 mutation.

In more detail, FIG. 1 illustrates a PCR product (1) obtained from amplification of a wild type reference nucleic acid sample. The PCR product includes a mutation site (2), which is wild type, and therefore has an adenine residue on the coding strand (3) and a thymine residue on the complementary strand (4). PCR product (1) is mixed with PCR product (5) obtained from amplification of a nucleic acid sample of interest. PCR product (5) has a mutation at mutation site (6), and has a cytidine residue on the coding strand (7) (instead of an adenine) and a guanine residue on the complementary strand (8) (instead of a thymine). The strands of PCR products (1) and (5) separate as they are heated and anneal again as they are gradually cooled. As a result, four different duplexes are formed, corresponding to different possible combinations of the four strands in the reaction. The two duplexes corresponding to the original PCR products (1) and (5) will re-anneal. These are homoduplexes—ie. they do not have a mismatched residue at the mutation site. However, new duplexes (9) will form that each contain coding strand (3) of PCR product (1) and complementary strand (8) from PCR product (5). Other new duplexes (10) will form that each contain coding strand (7) of PCR product (5) and complementary strand (4) of PCR product (1). The new duplexes (9) and (10) will be heteroduplexes—ie. they have a mismatched residue at the mutation site. Heteroduplexes (9) and (10) can then be detected, the presence of heteroduplexes indicating that the sample of interest contains mutant target nucleic acid.

FIG. 2 illustrates the present detection method. In steps A and B, target double stranded wild type DNA (100), comprising first DNA strand (120), and the complementary strand thereof (125), having a mutation site (105—indicated by the black spot) is mixed with reverse detection primer (110) at a high annealing temperature. Reverse detection primer (110) is a mutant detection primer—ie. the residue (115) in detection primer (110) that corresponds to mutation site (105) in the template is mutant. First DNA strand (120), and the complementary strand thereof (125), are separated by heating at high temperature, and then detection primer (110) binds to the first DNA strand (120). Detection primer (110) is extended along first DNA strand (120), thus generating second DNA strand (130). In further amplification cycle C, first DNA strand (120) and second DNA strand (130) are separated and another round of amplification is carried out using detection primer (110) thus generating more second DNA strand (130). Further amplification cycles D and E are carried out at a lower annealing temperature, at which forward and reverse amplification primer (not shown) bind to the target nucleic acid at a position away from mutation site (105). The forward amplification primer binds to second DNA strand (130) and to the complementary strand (125) and is extended to form a third DNA strand (135) that is complementary to the second DNA strand (130), and an additional copy of the first DNA strand (120). The reverse amplification primer binds to the first DNA strand and to the third DNA strand and is extended to form additional copies of the complementary strand (125), and the second DNA strand (130). Thus, after several rounds of amplification using the detection primer (110) and the forward and reverse amplification primers, multiple copies of strands (120, 125, 130 and 135) are generated in the reaction vessel.

FIG. 3 illustrates the results of the detection method of one embodiment of the present invention. Samples A-J are either wild type at the katG315 mutation site (samples A-E) or mutant at the katG315 mutation site (samples F-J). The samples were amplified as described in Example 1 using a mutant detection primer, duplexes were allowed to form and the duplex products applied to a dHPLC column, producing the elution profile of FIG. 3. Samples F, H, I and J all produced a one-peak elution profile—ie. no heteroduplexes present—thus confirming that they are mutant samples. Samples A-E all produced a 3-peak elution profile—ie. heteroduplexes present—thus confirming that these are wild type samples.

FIG. 4 illustrates elution profiles obtained from PCR products (amplified katG315 mutant and wild type samples) A-J that have been mixed to produce duplexes, as per the prior art detection method. The presence of heteroduplexes (3-peak pattern) illustrates that one strand comes from a wild type sample and one from a mutant sample (eg. A+H). The absence of heteroduplexes (one-peak pattern) illustrates that both stands come from a wild type sample (eg. A+B) or from a mutant sample. (eg. F+H).

FIG. 5 illustrates a region of the wild type KatG gene surrounding the Ser315 mutation site. The 20 nucleotide sequence within KatG to which forward amplification primer A binds is illustrated in pale typeface and italics. The 18 nucleotide sequence within KatG to which reverse amplification primer B binds is also illustrated in pale typeface and italics. The longer, 28 nucleotide, sequence to which the reverse detection primer C binds, is illustrated below (in the mutant version). The sequence to which the reverse detection primer binds overlaps with the sequence to which the reverse amplification primer binds. In this regard, whereas the detection primer binds to the residue at the mutation site (underlined in the KatG sequence and in the detection primer binding sequence), the amplification primer does not. Note that the nucleotide residue at the mutation site is a guanine in the wild type KatG gene sequence and is a cytosine in the mutant KatG gene.

EXAMPLES

Example 1

Detection of a Mutation in the *M. tuberculosis* katG Gene

Figure 1:
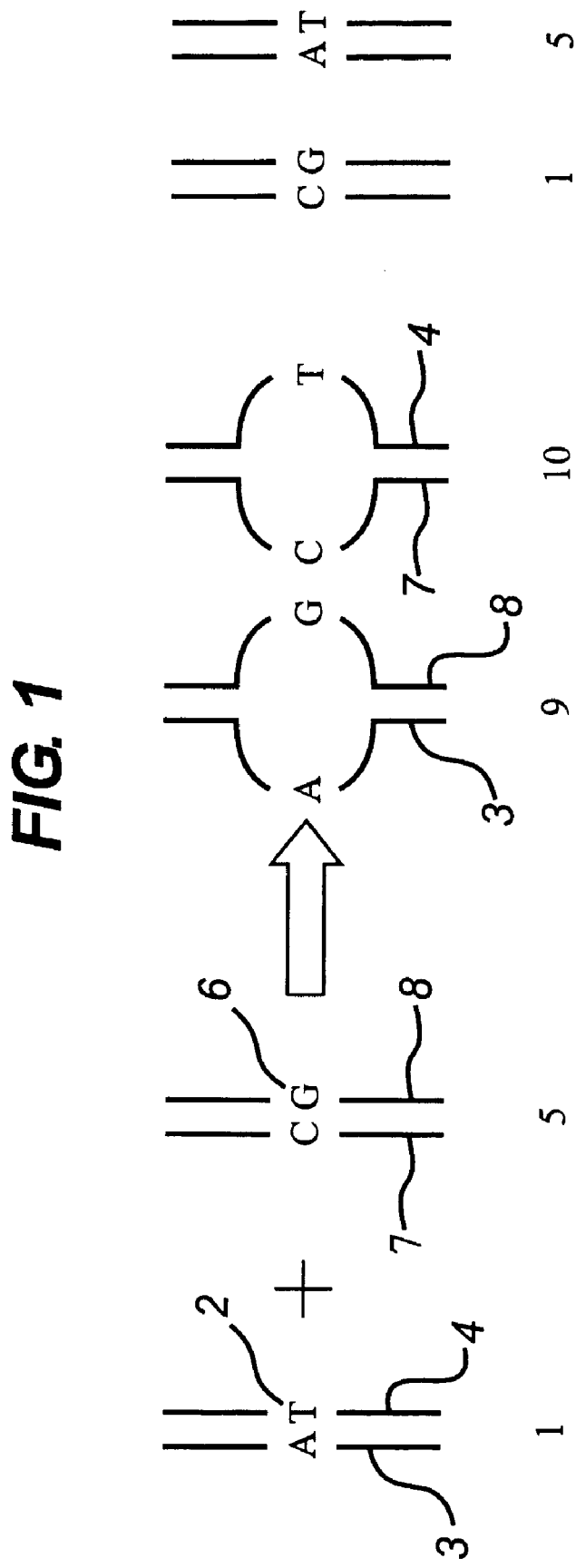
FIG. 1 illustrates the theory of a prior art dHPLC method for detecting a nucleic acid mutation.
Figure 2:
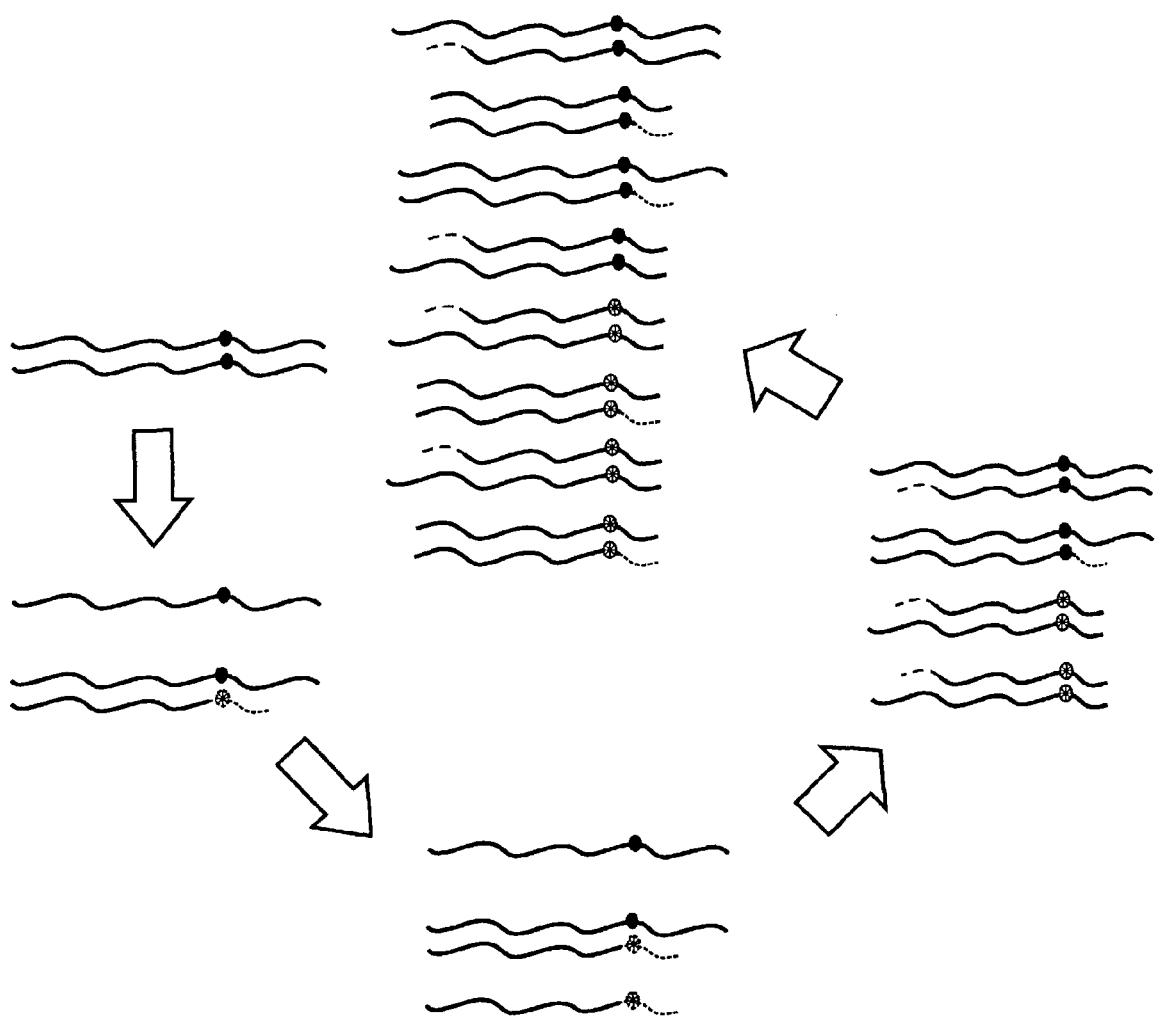
FIG. 2 illustrates the principle of the present detection method.
Figure 3:
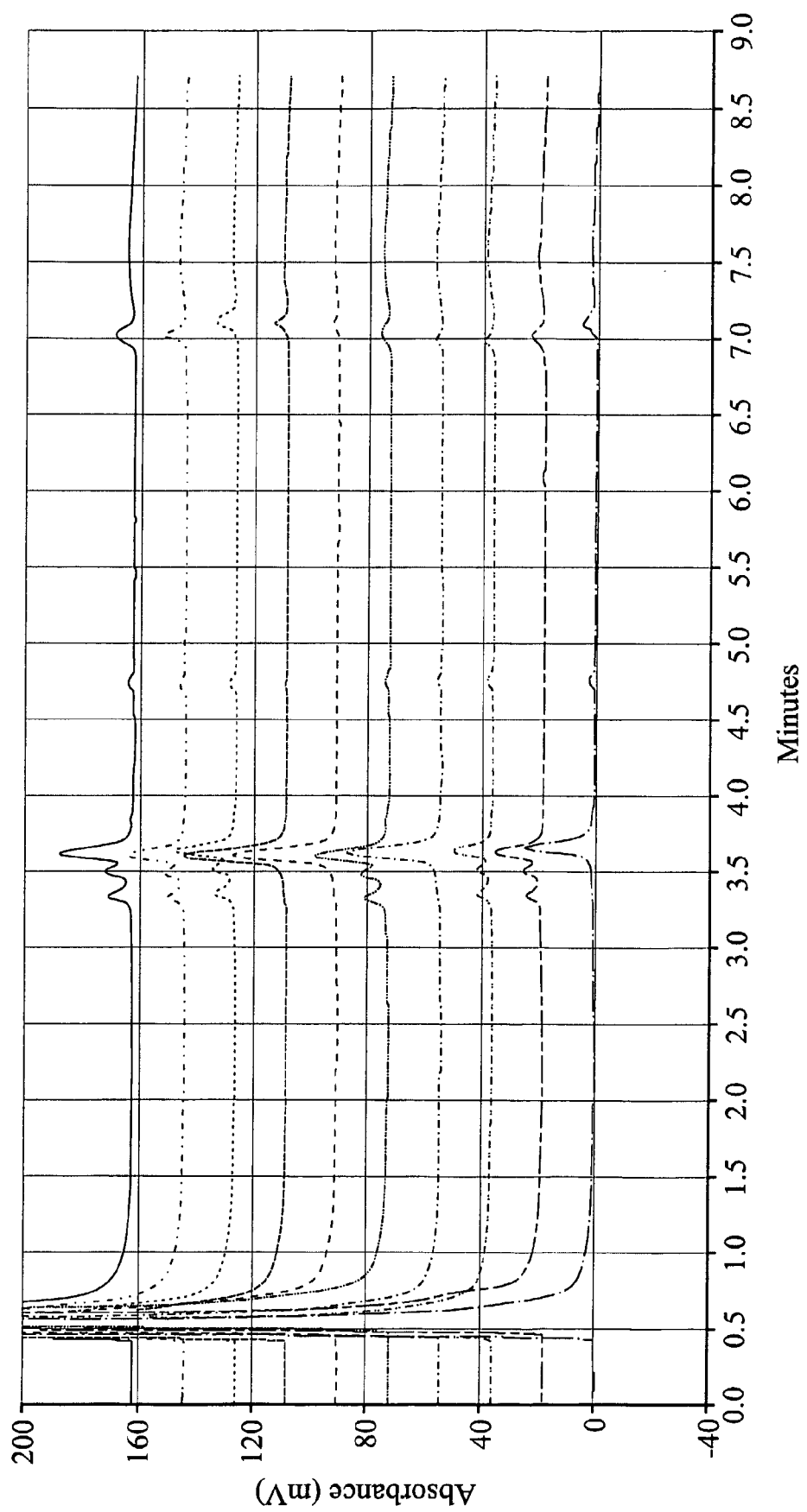
FIG. 3 illustrates the elution profile (dHPLC graph) obtained for mutant and wild type katG315 samples amplified using PCR according to one embodiment of the present detection method, described in Example 1.
Figure 4:
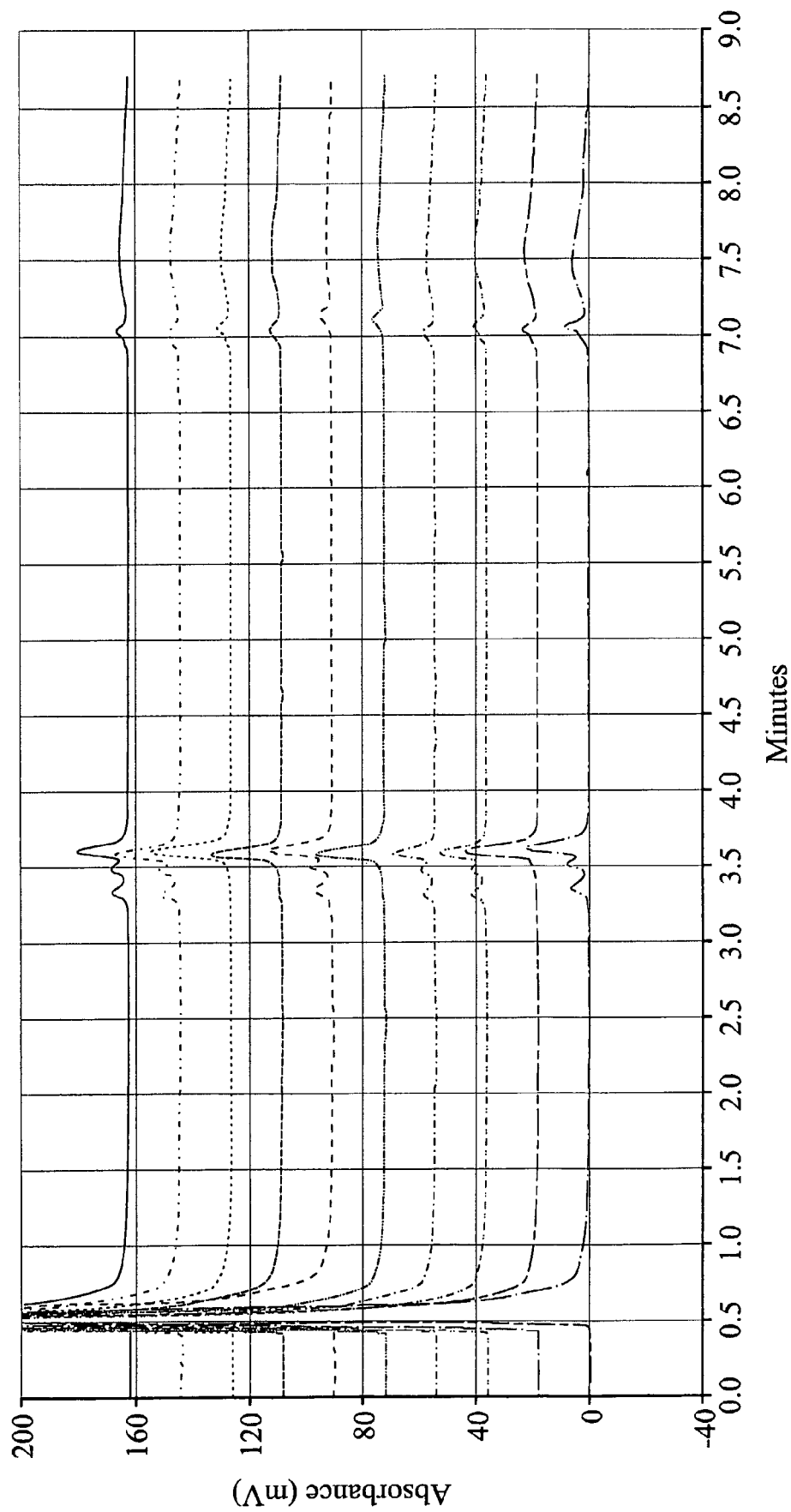
FIG. 4 illustrates the elution profile (dHPLC graph) obtained for mixtures of mutant and wild type katG315 samples prepared according to the prior art detection method.

The following comparative example compares the new and known detection methods in detail, with regard to detection of a mutation in the katG gene conferring isoniazid resistance to *M. tuberculosis* strains. Ten DNAs were examined, five with the mutation and five without:

Materials and Methods
Materials
PCR machine: GeneAmp7 PCR System 9700 (Applied Biosystems, Perkin Elmer UK, Beaconsfield, Bucks, UK)

PCR tubes for GeneAmp7 PCR System 9700 (Applied Biosystems, Perkin Elmer UK, Beaconsfield, Bucks, UK)

Denaturing High-Performance Liquid Chromatography/WAVE System (Transgenomic7, Ltd)

Reagents

DNA template: Five isolates containing the wild type katG Ser315 {A, B, C, D and E} and five isolates with a mutated katG-Ser315 {F, G, H, I and J}

Transgenomic Optimase7 Polymerase (Transgenomic7, Ltd)

10× Reaction Buffer with 1.5 mM $MgSO_4$ (Transgenomic7, Ltd)

dNTPs

PCR primers (Table I)

High purity water (Sigma)

WAVE Optimized J Buffer A, WAVE Optimized J Buffer B, WAVE OptimizedJ Syringe Wash Solution and WAVE Optimized J Solution D (Transgenomic7 Bioconsumables J, Ltd)

TABLE 1

| Primers | | | | |
|---|---|---|---|---|
| Primer name | Primer type | Primer sequence | SEQ ID NO: | $T_m$ |
| katGSer315 Fw | Amplification | 5'-c ggt cac act ttc ggt aag a-3' | 7 | $T_m$ = +/− 60° C. |
| katG315S RvI | Amplification | 5'-cat acg acc tcg atg ccg-3' | 8 | $T_m$ = 58.2° C. |
| katG315S RvII | Detection (mt) | 5'-cat acg acc tcg atg ccg <u>g</u>tg gtg atc g-3' | 4 | $T_m$ = 71.0° C. |

Methods

PCR:

| Each PCR reaction (new method): | Each PCR reaction (old method): |
|---|---|
| 1 μl Optimase Polymerase<br>1 μl dNTPs<br>5 μl 10× Reaction Buffer<br>2 μl katG_Ser315_Fw primer<br>2 μl katG315S*Rv_I primer<br>0.2 μl katG315S*Rv_II primer<br>36.8 μl $H_2O$<br>+2 μl DNA | 1 μl Optimase Polymerase<br>1 μl dNTPs<br>5 μl 10× Reaction Buffer<br>2 μl katG_Ser315_Fw primer<br>2 μl katG315S*Rv_I primer<br>37 μl $H_2O$<br>+2 μl DNA |
| PCR condition (new method) | PCR condition (old method) |
| 94° C. 2 mins<br>94° C. 30 seconds × 2<br>69° C. 30 seconds × 2<br>72° C. 90 seconds × 2<br>94° C. 30 seconds × 30<br>58° C. 30 seconds × 30<br>72° C. 1 min × 30<br>72° C. 10 mins<br>94° C. 5 mins<br>93.8° C. 8 seconds × 69*<br>93.6° C. 8 seconds × 69*<br>93.4° C. 8 seconds × 69*<br>93.2° C. 8 seconds × 69*<br>93° C. 8 seconds × 69*<br>25° C. 4 | 94° C. 2 mins<br>94° C. 30 seconds × 2<br>69° C. 30 seconds × 2<br>72° C. 90 seconds × 2<br>94° C. 30 seconds × 30<br>58° C. 30 seconds × 30<br>72° C. 1 min × 30<br>72° C. 10 mins<br>25° C. 4<br>Stopped, cooled down till room temperature and combined PCR products and followed by heteroduplex formation as per FIG. 1. |

Use PCR products immediately or freeze.
*Each cycle 1° C. lower than previous cycle dHPLC:

5 μl of the PCR products was applied to the DHPLC.

Method at 64.2° C.:

| Gradient Name | Time (mins) | % A | % B |
|---|---|---|---|
| Loading | 0 | 53.7 | 46.3 |
| Start Gradient | 0.5 | 48.7 | 51.3 |
| Stop Gradient | 5 | 39.7 | 60.3 |
| Start Clean | 5.1 | 0 | 100 |
| Stop Clean | 5.6 | 0 | 100 |
| Start Equilibrate | 5.7 | 53.7 | 46.3 |
| Stop Equilibrate | 6.6 | 53.7 | 46.3 |

Estimated Run Time: 8.7 minutes
Results The main products obtained during PCR using the present detection method were eluted around 3.0-4.0 minutes (FIG. 3). This retention time correlates with the retention time of the main products obtained by the old method (FIG. 4).

According to the sequencing data, samples A, B, C, D and E are wild type at the katG-Ser315 mutation site, and should therefore form heteroduplexes, because the detection primer covering the SNP has a mutated base at the katG-Ser315 mutation site. Samples F, H, I and J have a mutated katG-Ser315 and should therefore not form heteroduplexes, because the detection primer also has a mutated base.

Samples F, H, I and J have one main peak around 3.0-4.0 minutes, which suggest that those samples have a mutated katG-Ser315; the others, A, B, C, D and E have a three-peak pattern, which suggest that those samples have the wild type katG-Ser315. This correlates with the sequencing data.

Note that the following patterns are identical: wild type katG315 samples amplified according to the present detection method using a mutant detection primer generate a three peak pattern in the dHPLC graph, and this peak pattern is the same as for heteroduplexes obtained by mixing two PCR products, one mutated and one wild type katG315 (ie. old method).

Likewise, mutant katG315 samples amplified according to the present detection method using a mutant detection primer generate one main peak in the dHPLC graph, and this peak pattern is identical to that obtained by mixing two PCR products, either both mutated or both wild type katG315 (ie. old method).

Conclusions and Discussion

The present detection method enables detection of heteroduplexes, and hence known mutations, without the need for a different template DNA, quantifying PCR products or looking at multiple SNPs. The method takes just 8.7 minutes per sample, and it is likely that samples could be multiplexed (ie. more than one reaction per tube). Moreover, the present method does not require the use of special labelled primers, and there is no post-PCR processing as the PCR products can be immediately applied to the dHPLC.

Example 2
Detection of *Salmonella* Mutations

Mutations in the GyrA, GyrB, ParC and ParE topoisomerase genes are known to confer fluoroquinolone resistance in *Salmonella* (Randall et al. J. Antimicrob. Chemother. 2005; 56: 619-623). The following table shows the mutations involved, which are located in the Quinolone Resistance Determining Region (QRDR). The most common substitutions in gyrA result in a mutation at $Asp_{87}$ or $Ser_{83}$ of the translated polypeptide.

(A) Amino acid and nucleotide sequences of the QRDR of *S. enterica* gyrA.
(B) Sequences of probes used to identify the QRDR sequence.

TABLE

| | | |
|---|---|---|
| A | HisProHisGlyAspSerAlaValTyrAspThrIleValArgMetAla 5'-CATCCCCACGGCGATTCCGCAGTGTATGACACCATCGTTCGTATGGCG<br>-------+---------+---------+---------+---------+<br>GTAGGGGTGCCGCTAAGGCGTCACATACTGTGGTAGCAAGCATACCGC-5' | |
| B | WT | CGTCACATACTGTGGTAGC-5' |
| | $Asp_{87} \rightarrow Gly$ | GTCACATACCGTGGTAGCA-5' |
| | $Asp_{87} \rightarrow Ala$ | GTCACATACGGTGGTAGCA-5' |
| | $Asp_{87} \rightarrow Tyr$ | CGTCACATAATGTGGTAGCA-5' |
| | $Asp_{87} \rightarrow Asn$ | CGTCACATATTGTGGTAGCA-5' |
| | GTGCCGCTAAGGCGTCAC-5' | WT |
| | GTGCCGCTAAAGCGTCAC-5' | $Ser_{83} \rightarrow Phe$ |
| | GTGCCGCTAATGCGTCAC-5' | $Ser_{83} \rightarrow Tyr$ |
| | GTAGGGGTGACGCTAAGG-5' | $Gly_{81} \rightarrow Cys$ |

Primers designed in accordance with the present invention are used to detect the mutations as described above in Example 1.

5 μl of the PCR products is applied to the DHPLC as per Example 1. Run times are optimized once the assay is running (depending on the primers used and the particular mutation being detected) but alternative examples are as follows:

64.6° C. Estimated Run Time: 8.3 minutes

| Gradient Name | Time (mins) | % A | % B |
|---|---|---|---|
| Loading | 0 | 56.1 | 43.9 |
| Start Gradient | 0.1 | 51.1 | 48.9 |
| Stop Gradient | 4.6 | 42.1 | 57.9 |
| Start Clean | 4.7 | 0 | 100 |
| Stop Clean | 5.2 | 0 | 100 |
| Start Equilibrate | 5.3 | 56.1 | 43.9 |
| Stop Equilibrate | 6.2 | 56.1 | 43.9 |

63.4° C. Estimated Run Time: 8.7 minutes

| Gradient Name | Time (mins) | % A | % B |
|---|---|---|---|
| Loading | 0 | 52.7 | 47.3 |
| Start Gradient | 0.5 | 47.7 | 52.3 |

-continued

| Gradient Name | Time (mins) | % A | % B |
|---|---|---|---|
| Stop Gradient | 5 | 38.7 | 61.3 |
| Start Clean | 5.1 | 0 | 100 |
| Stop Clean | 5.6 | 0 | 100 |
| Start Equilibrate | 5.7 | 52.7 | 47.3 |
| Stop Equilibrate | 6.6 | 52.7 | 47.3 |

63.4° C. Estimated Run Time: 8.7 minutes

| Gradient Name | Time (mins) | % A | % B |
|---|---|---|---|
| Loading | 0 | 50.1 | 49.9 |
| Start Gradient | 0.5 | 45.1 | 54.9 |
| Stop Gradient | 5 | 36.1 | 63.9 |
| Start Clean | 5.1 | 0 | 100 |
| Stop Clean | 5.6 | 0 | 100 |
| Start Equilibrate | 5.7 | 50.1 | 49.9 |
| Stop Equilibrate | 6.6 | 50.1 | 49.9 |

The invention claimed is:

1. A method for detecting a mutation in a target nucleic acid sequence in a sample, the target nucleic acid sequence comprising a first DNA strand and optionally the complementary strand thereof, said method comprising:
   (a) adding a detection primer to the nucleic acid, wherein the detection primer binds to the first DNA strand at a DNA sequence that comprises the mutation site, wherein the detection primer is capable of binding to said DNA sequence and being extended regardless of whether or not there is a mutation at the mutation site;
   (b) extending the detection primer to form second DNA strands that are complementary to the first DNA strand;
   (c) adding an amplification primer to the nucleic acid, wherein the amplification primer binds to the second DNA strand and/or to the complementary strand, at a position away from the mutation site;
   (d) extending the amplification primer to form third DNA strands that are complementary to the second DNA strands, and/or additional copies of the first DNA strand;
   (e) annealing the DNA strands by complementary base pairing, to form nucleic acid duplexes, wherein if the two strands of the duplex have a mismatched residue at the mutation site, the duplex is a heteroduplex, and wherein if the two strands of the duplex do not have a mismatched residue at the mutation site, the duplex is a homoduplex; and
   (f) detecting the presence of heteroduplexes and/or homoduplexes.

2. A method according to claim 1, wherein step (d) further comprises adding a third primer that binds to the first DNA strand and/or to the third DNA strand at a position away from the mutation site, and extending said third primer to form additional copies of the complementary strand and/or the second DNA strand;
   wherein, if the detection primer is a reverse primer, the third primer is a reverse amplification primer; or
   wherein, if the detection primer is a forward primer, the third primer is a forward amplification primer.

3. A method according to claim 2, wherein the detection primer is a reverse primer, the amplification primer is a forward primer, and the third primer is a reverse amplification primer.

4. A method according to claim 2, wherein the detection primer is a forward primer, the amplification primer is a reverse primer, and the third primer is a forward amplification primer.

5. A method according to claim 1, wherein steps (a) to (d) are carried out sequentially.

6. A method according to claim 1, wherein steps (a) and (c) are carried out simultaneously.

7. A method according to claim 6, wherein steps (b) and (d) are carried out simultaneously.

8. A method according to claim 1, wherein the detection primer is a wild type detection primer, comprising a nucleic acid residue complementary to a wild type residue at the mutation site in the first DNA strand, and wherein the presence of heteroduplexes indicates that the sample contains target nucleic acid having a mutant residue at the mutation site.

9. A method according to claim 1, wherein the detection primer is a mutant detection primer, comprising a nucleic acid residue complementary to a mutant residue at the mutation site in the first DNA strand, and wherein the presence of heteroduplexes indicates that the sample contains target nucleic acid having a wild type residue at the mutation site.

10. A method according to claim 1, wherein the mutation is a nucleic acid substitution, deletion or insertion.

11. A method according to claim 1, wherein the detecting of the mutation in the target nucleic acid sequence comprises detecting multiple mutations in the target nucleic acid sequence selected from the group consisting of nucleic acid substitutions, deletions and insertions.

12. A method according to claim 1, wherein the extending steps are carried out by PCR.

13. A method according to claim 1, wherein the detection of heteroduplexes and/or homoduplexes is carried out by denaturing high-performance liquid chromatography.

14. A method according to claim 1, wherein the detection primer is at least 15 nucleotides long.

15. A method according to claim 14, wherein the detection primer is at least 20 nucleic acids long.

16. A method according to claim 1, wherein the detection primer has a higher melting temperature than the amplification primer.

17. A method according to claim 16, wherein step (a) is carried out at a high annealing temperature, at which the detection primer can bind to the target nucleic acid but the amplification primer can not bind to the target nucleic acid.

18. A method for detecting a mutation in a target nucleic acid sequence in a sample, the target nucleic acid sequence comprising a first DNA strand and optionally the complementary strand thereof, said method comprising:
(a) adding a detection primer to the nucleic acid, wherein the detection primer binds to the first DNA strand at a DNA sequence that comprises the mutation site, wherein the detection primer is capable of binding to said DNA sequence and being extended regardless of whether or not there is a mutation at the mutation site;
(b) extending the detection primer to form second DNA strands that are complementary to the first DNA strand;
(c) adding an amplification primer to the nucleic acid, wherein the amplification primer binds to the second DNA strand and/or to the complementary strand, at a position away from the mutation site;
(d) extending the amplification primer to form third DNA strands that are complementary to the second DNA strands, and/or additional copies of the first DNA strand;
(e) annealing the DNA strands by complementary base pairing, to form nucleic acid duplexes, wherein if the two strands of the duplex have a mismatched residue at the mutation site, the duplex is a heteroduplex, and wherein if the two strands of the duplex do not have a mismatched residue at the mutation site, the duplex is a homoduplex; and
(f) detecting the presence of heteroduplexes and/or homoduplexes;
wherein the detection primer has a higher melting temperature than the amplification primer.

19. A method for detecting a mutation in a target bacterial or viral nucleic acid sequence in a sample, the target nucleic acid sequence comprising a first DNA strand and optionally the complementary strand thereof, said method comprising:
(a) adding a detection primer to the nucleic acid, wherein the detection primer binds to the first DNA strand at a DNA sequence that comprises the mutation site, wherein the detection primer is capable of binding to said DNA sequence and being extended regardless of whether or not there is a mutation at the mutation site;
(b) extending the detection primer to form second DNA strands that are complementary to the first DNA strand;
(c) adding an amplification primer to the nucleic acid, wherein the amplification primer binds to the second DNA strand and/or to the complementary strand, at a position away from the mutation site;
(d) extending the amplification primer to form third DNA strands that are complementary to the second DNA strands, and/or additional copies of the first DNA strand;
(e) annealing the DNA strands by complementary base pairing, to form nucleic acid duplexes, wherein if the two strands of the duplex have a mismatched residue at the mutation site, the duplex is a heteroduplex, and wherein if the two strands of the duplex do not have a mismatched residue at the mutation site, the duplex is a homoduplex; and
(f) detecting the presence of heteroduplexes and/or homoduplexes.

20. A method according to claim 17, wherein step (c) is carried out at a lower annealing temperature than step (a), at which lower temperature the amplification primer can bind to the target nucleic acid.

21. A method according to claim 8, comprising repeating steps (a) to (e) using a mutant detection primer, comprising a nucleic acid residue that is complementary to a mutant residue at the mutation site in the first DNA strand, and wherein the presence of heteroduplexes indicates that the sample contains a mixture of wild type and mutant target nucleic acid.

22. A method according to claim 9, comprising repeating steps (a) to (e) using a wild type detection primer, comprising a nucleic acid residue that is complementary to a wild type residue at the mutation site in the first DNA strand, and wherein the presence of heteroduplexes indicates that the sample contains a mixture of wild type and mutant target nucleic acid.

23. A method according to claim 1, wherein the target nucleic acid is single stranded.

24. A method according to claim 1, wherein the target nucleic acid is RNA, and is converted into cDNA prior to step (a).

25. A method according to claim 1, wherein the sample is a clinical sample.

26. A method according to claim 1, wherein the target nucleic acid is from a mycobacterium species.

27. A method according to claim 26, wherein the target nucleic acid comprises the nucleic acid sequence SEQ ID NO: 1.

28. A method according to claim 27, wherein the detection primer binds to a DNA sequence that is at least 80% identical to SEQ ID NO: 2, or to the complement thereof.

29. A method according to claim 27, wherein the detection primer is a wild type detection primer comprising the sequence of SEQ ID NO: 3, or a sequence having at least 80% identity thereto, with the proviso that residue 19 of said sequence is cytosine.

30. A method according to claim 27, wherein the detection primer is a mutant detection primer comprising the sequence of SEQ ID NO: 4, or a sequence having at least 80% identity thereto, with the proviso that residue 19 of said sequence is guanine.

31. A method according to claim 1, wherein the target nucleic acid is from an aerobic bacterium.

32. A method according to claim 1, wherein the target nucleic acid is from a facultative anaerobic bacterium.

33. A method according to claim 1, wherein the target nucleic acid is from a Gram +ve bacterium.

34. A method according to claim 1, wherein the target nucleic acid is from a Gram −ve bacterium.

35. A method according to claim 1, wherein the target nucleic acid is from an enterobacterium.

36. A method according to claim 1, wherein the target nucleic acid is from a *Bacillus, Neisseria* or *Salmonella* species.

37. A method according to claim 1, wherein the target nucleic acid is from *B. cereus, B. subtilis, N. meningitides, M. tuberculosis* or *S. enterics*.

* * * * *

UNITED STATES PATENT AND TRADEMARK OFFICE
CERTIFICATE OF CORRECTION

| | |
|---|---|
| PATENT NO. | : 7,935,480 B2 |
| APPLICATION NO. | : 11/722703 |
| DATED | : May 3, 2011 |
| INVENTOR(S) | : Catherine Arnold |

It is certified that error appears in the above-identified patent and that said Letters Patent is hereby corrected as shown below:

Title Page 2, Item (56)

Col. 2, Line 1, please delete "swquence" and insert --sequence--.

Signed and Sealed this
Twenty-ninth Day of November, 2011

David J. Kappos
*Director of the United States Patent and Trademark Office*